United States Patent [19]

Schirmer et al.

[11] Patent Number: 4,782,177

[45] Date of Patent: Nov. 1, 1988

[54] ACRYLIC ACID DERIVATIVES AND FUNGICIDES WHICH CONTAIN THESE COMPOUNDS

[75] Inventors: Ulrich Schirmer, Heidelberg; Stefan Karbach, Ludwigshafen; Ernst-Heinrich Pommer, Limburgerhof; Eberhard Ammermann, Ludwigshafen; Wolfgang Steglich, Bonn-Roettgen; Barbara A. M. Schwalge, Lohmar; Timm Anke, Kaiserslautern, all of Fed. Rep. of Germany

[73] Assignee: BASF Aktiengesellschaft, Rheinland-Pfalz, Fed. Rep. of Germany

[21] Appl. No.: 941,323

[22] Filed: Dec. 15, 1986

[30] Foreign Application Priority Data

Dec. 20, 1985 [DE] Fed. Rep. of Germany ....... 3545318

[51] Int. Cl.$^4$ ............................................. C07C 69/76
[52] U.S. Cl. .................... 560/060; 560/009; 560/011; 560/012; 560/014; 560/023; 560/029; 560/034; 560/056; 558/012; 558/414; 71/107
[58] Field of Search .............. 560/060, 009, 011, 012, 560/014, 023, 029, 034, 056; 558/012, 414

[56] References Cited

U.S. PATENT DOCUMENTS

3,639,445  2/1972  Pawloski ............................ 560/660

FOREIGN PATENT DOCUMENTS

0178826  4/1986  European Pat. Off. .

OTHER PUBLICATIONS

Chemical Week, Jun. 21, 1972, p. 46.
Chemische Berichte, vol. III, pp. 2779–2784 (1978).

*Primary Examiner*—Paul J. Killos

*Attorney, Agent, or Firm*—Oblon, Fisher, Spivak, McClelland & Maier

[57] ABSTRACT

Acrylic acid derivatives of the general formula

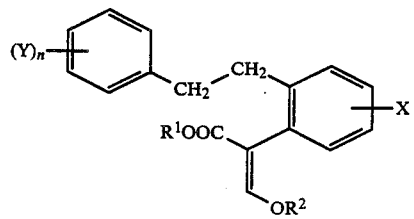

where $R^1$ and $R^2$ independently of one another are each alkyl, X is hydrogen, halogen, alkoxy, trifluoromethyl, cyano or nitro, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, $NO_2$, alkylthio, thiocyanato, cyano,

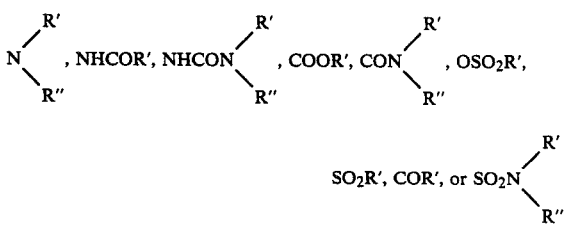

R' and R" independently of one another are each hydrogen, alkyl, alkoxy, alkylthio or cycloalkyl or are each unsubstituted or substituted phenyl, and n is from 1 to 4, and fungicides containing these compounds.

9 Claims, No Drawings

ACRYLIC ACID DERIVATIVES AND FUNGICIDES WHICH CONTAIN THESE COMPOUNDS

The present invention relates to novel acrylic acid derivatives and fungicides which contain these compounds.

It is known that N-trichloromethylthiotetrahydrophthalimide can be used as a fungicide in agriculture, fruit cultivation and horticulture (Chem. Week, June 21, 1972, page 46). However, the known agent can only be used prior to infection and, at low application rates, its action does not meet the requirements set in practice.

We have found that novel acrylic acid derivatives of the formula

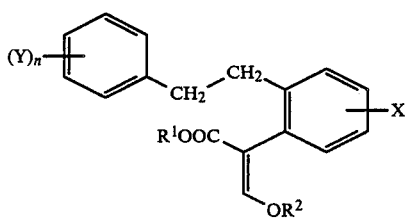

where $R^1$ and $R^2$ independently of one another are each $C_1$–$C_8$-alkyl, X is hydrogen, halogen, $C_1$–$C_4$-alkoxy, trifluoromethyl, cyano or nitro, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, $NO_2$, alkylthio, thiocyanato, cyano,

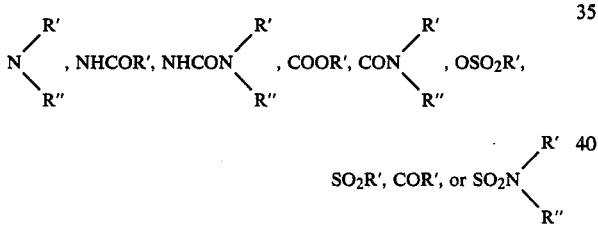

R' and R" independently of one another are each hydrogen, alkyl, alkoxy, alkylthio or cycloalkyl or are each phenyl which is unsubstituted or substituted by alkyl, halogen or alkoxy, and n is from 1 to 4, have an excellent fungicidal action.

The radicals mentioned in the general formula may have, for example, the following meanings: $R^1$ and $R^2$ are each straight-chain or branched $C_1$–$C_8$-alkyl (eg. methyl, ethyl, isopropyl, n-propyl, n-butyl, sec-butyl, tert-butyl, isobutyl, sec-pentyl, n-hexyl, α-ethyl-n-hexyl or n-octyl), X is hydrogen, halogen (eg. fluorine, chlorine or bromine), $C_1$–$C_4$-alkoxy (eg. methoxy or n-butoxy), trifluoromethyl, cyano or $NO_2$, Y is hydrogen, $C_1$–$C_{12}$-alkyl (eg. methyl, ethyl, tertbutyl or dodecyl), halo-$C_1$–$C_4$-alkyl (eg. trifluoromethyl), $C_1$–$C_4$-alkoxy-$C_1$–$C_4$-alkyl (eg. methoxymethyl), $C_5$–$C_8$-cycloalkyl (eg. cyclohexyl), aralkyl (eg. benzyl), aryl (eg. phenyl), aryloxy (eg. phenoxy), halogen (eg. fluorine, chlorine, bromine or iodine), and unsubstituted or substituted $C_4H_4$ chain which is fused to the benzene ring to form an unsubstituted or substituted naphthyl ring, $C_1$–$C_6$-alkoxy (eg. isopropoxy or hexyloxy), halo-$C_1$–$C_4$-alkoxy (eg. 1,1,2,2-tetrafluoroethoxy), $C_1$–$C_4$-alkylthio (eg. methylthio), thiocyanato, cyano, $NO_2$

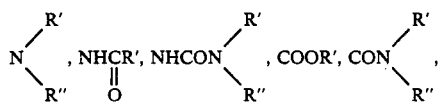

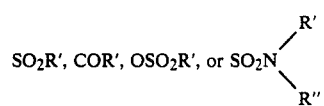

and R' and R" independently of one another are each hydrogen, $C_1$–$C_4$-alkyl (eg. methyl or ethyl), $C_1$–$C_4$-alkoxy (eg. methoxy or tert-butoxy), $C_1$–$C_4$-alkylthio (eg. methylthio) or $C_5$–$C_8$-cycloalkyl (eg. cyclohexyl) or are each phenyl which is unsubstituted or substituted by $C_1$–$C_4$-alkyl, halogen or $C_1$–$C_4$-alkoxy (eg. phenyl, 3-chlorophenyl 4-methylphenyl or 3-methoxyphenyl).

The novel compounds can be prepared, for example by the following process:

2-methylphenylacetates of the general formula

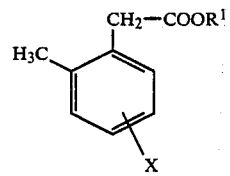

are reacted by the Wislicenus method (Liebigs Annalen 424 (1921), 215 and Ibid. 413 (1917), 206) with methyl formate and sodium hydride in an inert solvent. The resulting compounds of the general formula

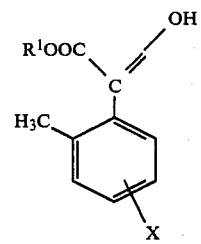

are reacted with an alkylating agent in the presence of a base in a solvent (eg. acetone) to give α-(2-methylphenyl)-β-alkoxyacrylates

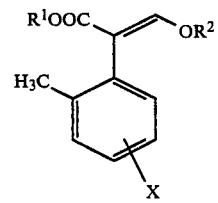

in which $R^1$, $R^2$ and X have the above meanings.

Bromination of this compound with N-bromosuccinimide (Horner and Winkelmann, Angew. Chem. 71 (1959), 349) Leads to α-(2-bromomethylphenyl)-β-alkoxyacrylates, which react with trialkyl phosphites to give phosphonates of the general formula

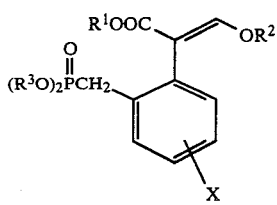

where $R^1$, $R^2$ and X have the above meanings and $R^3$ is $C_1$–$C_8$-alkyl (Houben-Weyl, Methoden der organischen Chemie 12/1, 433 et seq. (1963)).

The above phosphonates are reacted with unsubstituted or substituted benzaldehydes to give stilbene derivatives:

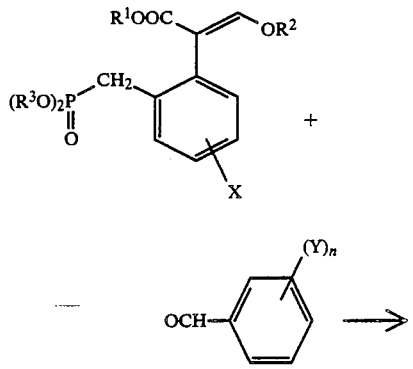

(cf. Wadsworth and Emmons, J. Amer. Chem. Soc. 83 (1961), 1732)

The resulting stilbene derivatives can be reduced catalytically and selectively with hydrogen (cf. Houben-Weyl, Methoden der organischen Chemie v/2b, 264–267 (1981) or with diimine (cf. Ibid. IV/1c, 580 and E. E. van Tamelen, R. S. Dewey, M. F. Lease and W. H. Pirkle, J. Amer. Chem. Soc. 83 (1961), 4302) to give the novel acrylic acid derivatives:

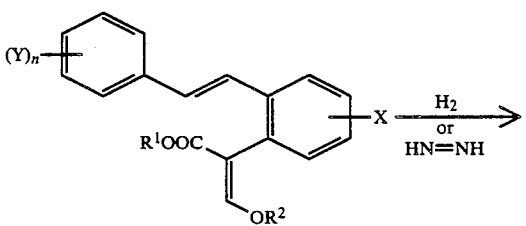

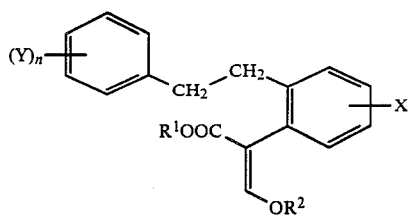

The methods below illustrate the synthesis of the starting compounds.

Method A

Methyl α-(2-methylphenyl)-β-methoxyacrylate 16.5 g of methyl 2-methylphenyl acetate are dissolved in 10 ml of methyl formate, and the solution is slowly added dropwise to a suspension of 3 g of sodium hydride in 150 ml of absolute ether. The mixture is refluxed for 4 hours, after which it is acidified with dilute HCl, and the organic phase is separated off, washed with water, dried over $MgSO_4$ and evaporated down to give 13.8 g of a pure yellow oil (methyl α-formyl-(2-methylphenyl)-acetate), which is refluxed with 5.8 ml of dimethylsulphate, 10.9 g of potassium carbonate and 70 ml of acetone for 1 hour. The mixture is filtered, the filtrate is evaporated down, the residue is taken up in ether, and the solution is then washed with dilute aqueous ammonia and several times with water. After the ether has been stripped off, 11.3 g of crude methyl α-(2-methyl-phenyl)-β-methoxyacrylate (Bp. 102°–108° C./0.05) are obtained.

| NMR in $CDCl_3$: | 7.53 | s 1H |
|---|---|---|
| | 7.16–7.36 broad | s 4H |
| | 3.64 | s 3H |
| | 3.73 | s 3H |
| | 2.16 | s 3H |

Method B

Methyl α-(2-bromomethylphenyl)-β-methoxyacrylate 20.6 g of the methyl α-(2-methylphenyl)-β-methoxyacrylate obtained as described in Method A, 17.65 g of bromosuccinimide, 0.2 g of azobisisobutyronitrile and 150 ml of $CCl_4$ are slowly heated to 90° C. and kept at this temperature until all the succinimide floats on the solvent. The mixture is filtered, the filtrate is evaporated down, the remaining oil is dissolved in about 5 ml of acetone and the solution is brought to crystallization with n-hexane. 27.5 g of colorless crystals of melting point 86°–87° C. are obtained.

Method C

Dimethyl 2-(β-methoxy-α-methoxycarbonylvinyl)benzylphosphonate 28.5 g of methyl α-(2-bromomethylphenyl)-β-methoxyacrylate are refluxed with 11.8 ml of trimethyl phosphite and 6.5 ml of toluene for one hour. The reaction mixture is carefully evaporated down under reduced pressure, the remaining oil is dissolved in 5 ml of ether, and the solution is then brought to crystallization with n-hexane. 27.3 g of colorless crystals of melting point 94° C. are obtained.

Method D

2-(β-methoxy-α-methoxycarbonylvinyl)-stilbene 3.14 g of dimethyl 2-(β-methoxy-α-methoxycarbonylvinyl)benzylphosphonate, dissolved in 7 ml of absolute tetrahydrofuran, are added dropwise, at 0° C. to 0.3 g of sodium hydride in 5 ml of absolute tetrahydrofuran. After from 20 to 30 minutes, 1.1 ml of benzaldehyde are added and the mixture is allowed to warm up to 20° C. and then refluxed for 5 hours. After cooling, it is evaporated down and 15 ml of water and 70 ml of ether are added. The organic phase is then extracted by shaking with 3×15 ml of 10% strength by weight aqueous NaHCO$_3$ solution and then extracted 3 times by shaking with saturated NaCl solution. The organic phase is dried over MgSO$_4$ and then evaporated down, and the residue is finally recrystallized from chloroform/hexane. 1.7 g of colorless crystals of 2-(β-methoxy-α-methoxycarbonylvinyl)stilbene of melting point 107°–109° C. are obtained.

The Example which follows illustrates the preparation of the novel compounds.

EXAMPLE 1

Methyl α-(2-phenethylphenyl)-β-methoxyacrylate 6 g of 2-(β-methoxy-α-methoxycarbonylvinyl)-stilbene in 150. ml of tetrahydrofuran are hydrogenated in the presence of 1 g of Pd/C (10% strength) under a hydrogen pressure of 1.05 bar and at 17°–21° C. After 0.4 l of hydrogen has been absorbed, the mixture is filtered and the filtrate is evaporated down. 5.3 g of white crystals of melting point 52°–54° C. are obtained (compound No. 1).

The following compounds may be obtained analogously:

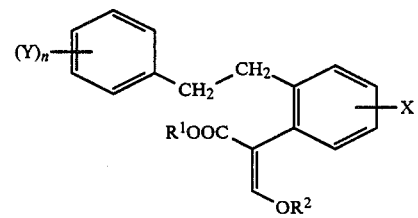

| No. | R$^1$ | R$^2$ | X | (Y)$_n$ | Mp °C./NMR |
|---|---|---|---|---|---|
| 1 | CH$_3$ | CH$_3$ | H | H | 52–54 |
| 2 | C$_2$H$_5$ | CH$_3$ | H | H | |
| 3 | i-C$_3$H$_7$ | CH$_3$ | H | H | |
| 4 | nC$_6$H$_{13}$ | CH$_3$ | H | H | |
| 5 | n-C$_4$H$_9$ | CH$_3$ | H | H | |
| 6 | n-C$_3$H$_7$ | CH$_3$ | H | H | |
| 7 | s-C$_4$H$_9$ | CH$_3$ | H | H | |
| 8 | CH$_3$ | C$_2$H$_5$ | H | H | |
| 9 | CH$_3$ | i-C$_3$H$_7$ | H | H | |
| 10 | CH$_3$ | n-C$_6$H$_{13}$ | H | H | |
| 11 | CH$_3$ | n-C$_3$H$_7$ | H | H | |
| 12 | CH$_3$ | s-C$_4$H$_9$ | H | H | |
| 13 | CH$_3$ | CH$_3$ | H | H | |
| 14 | CH$_3$ | CH$_3$ | 3-Cl | H | |
| 15 | CH$_3$ | CH$_3$ | 4-Cl | H | |
| 16 | CH$_3$ | CH$_3$ | 5-Cl | H | |
| 17 | CH$_3$ | CH$_3$ | 6-Cl | H | |
| 18 | CH$_3$ | CH$_3$ | 5-OCH$_3$ | H | |
| 19 | CH$_3$ | CH$_3$ | 5-CF$_3$ | H | |
| 20 | CH$_3$ | CH$_3$ | 5-CN | H | |
| 21 | CH$_3$ | CH$_3$ | 5-NO$_2$ | 4-CH$_3$ | |
| 22 | CH$_3$ | CH$_3$ | 6-NO$_2$ | H | |
| 23 | CH$_3$ | CH$_3$ | H | 4-t-C$_4$H$_9$ | |
| 24 | CH$_3$ | CH$_3$ | H | 4-C$_2$H$_5$ | |
| 25 | CH$_3$ | CH$_3$ | H | 4-CH$_3$ | |
| 26 | CH$_3$ | CH$_3$ | H | 2-CH$_3$ | |
| 27 | CH$_3$ | CH$_3$ | H | 3-CH$_3$ | 56–58 |
| 28 | CH$_3$ | CH$_3$ | H | 2-Cl | |
| 29 | CH$_3$ | CH$_3$ | H | 3-Cl | 45–48 |
| 30 | CH$_3$ | CH$_3$ | H | 4-Cl | |
| 31 | CH$_3$ | CH$_3$ | H | 2,4-Cl$_2$ | |
| 32 | CH$_3$ | CH$_3$ | H | 3,5-Cl$_2$ | |
| 33 | CH$_3$ | CH$_3$ | H | 2-F | |
| 34 | CH$_3$ | CH$_3$ | H | 3-F | |
| 35 | CH$_3$ | CH$_3$ | H | 4-F | |
| 36 | CH$_3$ | CH$_3$ | H | 3-CF$_3$ | 48–50 |
| 37 | CH$_3$ | CH$_3$ | H | 4-CF$_3$ | 83–87 |
| 38 | CH$_3$ | CH$_3$ | H | 4-Br | |
| 39 | CH$_3$ | CH$_3$ | H | 3-phenoxy | oil |
| 40 | CH$_3$ | CH$_3$ | H | 4-phenoxy | |
| 41 | CH$_3$ | CH$_3$ | H | 2-OCH$_3$ | 72–75 |
| 42 | CH$_3$ | CH$_3$ | H | 3-OCH$_3$ | 26–30 |
| 43 | CH$_3$ | CH$_3$ | H | 4-OCH$_3$ | |
| 44 | CH$_3$ | CH$_3$ | H | 4-O(t)-C$_4$H$_9$ | |
| 45 | CH$_3$ | CH$_3$ | H | 4-O(n)-C$_4$H$_9$ | |
| 46 | CH$_3$ | CH$_3$ | H | 4-CH$_2$OCH$_3$ | |
| 47 | CH$_3$ | CH$_3$ | H | 4-I | |

-continued

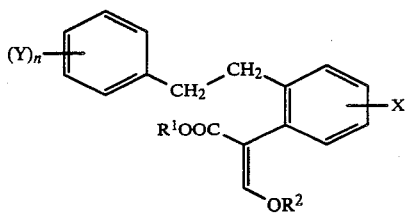

| No. | R¹ | R² | X | (Y)ₙ | Mp °C./NMR |
|---|---|---|---|---|---|
| 48 | CH₃ | CH₃ | H | 2,3 (fused benzene) | oil |
| 49 | CH₃ | CH₃ | H | 3,4 (fused benzene) | 92–93 |
| 50 | CH₃ | CH₃ | H | 4-OCHF₂ | |
| 51 | CH₃ | CH₃ | H | 3-OCF₂CHF₂ | |
| 52 | CH₃ | CH₃ | H | 4-SCH₃ | |
| 53 | CH₃ | CH₃ | H | 4-CN | |
| 54 | CH₃ | CH₃ | H | 3-CN | |
| 55 | CH₃ | CH₃ | H | 4-SCN | |
| 56 | CH₃ | CH₃ | H | 4-N(CH₃)₂ | |
| 57 | CH₃ | CH₃ | H | 3-NHCOCH₃ | |
| 58 | CH₃ | CH₃ | H | 3-NHCOOCH₃ | |
| 59 | CH₃ | CH₃ | H | 4-NHCON(CH₃)₂ | |
| 60 | CH₃ | CH₃ | H | 4-COOCH₃ | |
| 61 | CH₃ | CH₃ | H | 4-CONHCH₃ | |
| 62 | CH₃ | CH₃ | H | 4-SO₂CH₃ | |
| 63 | CH₃ | CH₃ | H | 4-phenylsulfonyl | |
| 64 | CH₃ | CH₃ | H | 3-COCH₃ | |
| 65 | CH₃ | CH₃ | H | 4-OSO₂CH₃ | |
| 66 | CH₃ | CH₃ | H | 4-SO₂N(CH₃)₂ | |
| 67 | CH₃ | CH₃ | H | 4-NHCONH-(3-chlorophenyl) | |
| 68 | CH₃ | CH₃ | H | 4-benzoyl | |
| 69 | CH₃ | CH₃ | H | 3-NO₂ | |
| 70 | CH₃ | CH₃ | H | 4-NO₂ | |
| 71 | CH₃ | CH₃ | H | 2-Cl-6F | |
| 72 | CH₃ | CH₃ | H | 2,4,5(CH₃)₃ | |
| 73 | CH₃ | CH₃ | H | 3,4,5(OCH₃)₃ | oil |
| 74 | CH₃ | CH₃ | H | 2,4(CH₃)₂ | |
| 75 | CH₃ | CH₃ | H | 4-i-C₃H₇ | |
| 76 | CH₃ | CH₃ | H | 4-phenyl | |
| 77 | CH₃ | CH₃ | H | 2,3,4-Cl₃ | |
| 78 | CH₃ | CH₃ | H | 2,6-Cl₂ | |
| 79 | CH₃ | CH₃ | H | 3,4-Cl₂ | |
| 80 | CH₃ | CH₃ | H | 3-NO₂4CH₃ | |
| 81 | CH₃ | CH₃ | H | 4-N(C₂H₅)₂ | |
| 82 | CH₃ | CH₃ | H | 2,4,5(OCH₃)₃ | |
| 83 | CH₃ | CH₃ | H | 3,5-(OCH₃)₂ | |
| 84 | CH₃ | CH₃ | H | 3-benzyloxy | oil |
| 85 | CH₃ | CH₃ | H | 2,4,6(OCH₃)₃ | |
| 86 | CH₃ | CH₃ | H | 4-O(n)C₆H₁₃ | |
| 87 | CH₃ | CH₃ | H | 2-Cl5NO₂ | |
| 88 | CH₃ | CH₃ | H | 3NO₂4Cl | |
| 89 | CH₃ | CH₃ | H | 2-Cl6NO₂ | |
| 90 | CH₃ | CH₃ | H | 2-OCF₂CHF₂ | |
| 91 | CH₃ | CH₃ | H | 3-Br4OCH₃ | |
| 92 | C₂H₅ | CH₃ | H | 3-Cl | |
| 93 | C₂H₅ | CH₃ | H | 4-Cl | |
| 94 | C₂H₅ | CH₃ | H | 3,5Cl₂ | |
| 95 | C₂H₅ | CH₃ | H | 4-F | |
| 96 | C₂H₅ | CH₃ | H | 4-Br | |
| 97 | C₂H₅ | CH₃ | H | 4-CH₃ | |

-continued

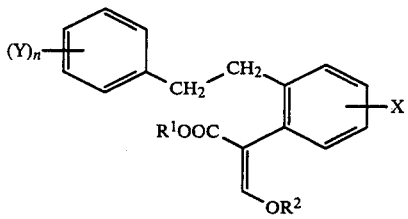

| No. | R¹ | R² | X | (Y)ₙ | Mp °C./NMR |
|---|---|---|---|---|---|
| 98 | C₂H₅ | CH₃ | H | 3,4-(CH₃)₂ | |
| 99 | C₂H₅ | CH₃ | H | 4-OCH₃ | |
| 100 | C₂H₅ | CH₃ | H | 3,4,5-(OCH₃)₃ | |
| 101 | C₂H₅ | CH₃ | H | 3-CH₃ | |
| 102 | C₂H₅ | CH₃ | H | 4-(t)C₄H₉ | |
| 103 | C₂H₅ | CH₃ | H | 2CH₃ | |
| 104 | CH₃ | C₂H₅ | H | 4-Cl | |
| 105 | CH₃ | C₂H₅ | H | 4-F | |
| 106 | CH₃ | C₂H₅ | H | 4-CH₃ | |
| 107 | CH₃ | C₂H₅ | H | 4-OCH₃ | |
| 108 | CH₃ | C₂H₅ | H | 4-NO₂ | |

In general terms, the novel compounds are very effective against a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and for vegetables, such as cucumbers, beans and Cucurbitaceae.

The novel compounds are particularly useful for controlling the following plant diseases:
*Erysiphe graminis* in cereals,
*Erysiphe cichoracearum* and *Sphaerotheca fuliginea* in Cucurbitaceae,
*Podosphaera leucotricha* in apples,
*Uncinula necator* in vines,
*Puccinia* species in cereals,
*Rhizoctonia solani* in cotton and lawns,
*Ustilago* species in cerals and sugar cane,
*Venturia inaequalis* (scab) in apples,
*Septoria nodorum* in wheat,
*Pyrenophora teres* in barley,
*Botrytis cinerea* (gray mold) in strawberries and vines,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Alternaria solani* in potatoes and tomatoes,
*Plasmopara viticola* in grapes, and
Fusarium and Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The application forms depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (eg. xylene or benzene), chlorinated aromatics (eg. chlorobenzenes), paraffins (eg. oil fractions), alcohols (eg. methanol or butanol), ketones (eg. cyclohexanone), amines (eg. ethanolamine or dimethylformamide) and water; carriers, such as ground natural minerals (kaolins, aluminas, talc or chalk) and ground synthetic minerals (eg. highly disperse silica or silicates); emulsifiers, such as nonionic and anionic emulsifiers (eg. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient. The application rates are from 0.05 to 3 kg or more of active ingredient per ha, depending on the type of effect desired.

The novel compounds may also be employed in material protection, inter alia for controlling wood-destroying fungi, such as *Coniophora puteana* and *Polystictus versicolor*. The novel active ingredients can also be used as fungicidal components of oily wood preservatives for protecting wood against wood-discoloring fungi. They are used by treating, for example impregnating or painting, the wood with these agents.

Some of the novel compounds are extremely effective against human-pathogenic fungi, such as *Trichophyton mentagrophytes* and *Candida albicans*. The agents and the ready-to-use formulations prepared from them, such as solutions, emulsions, suspensions, powders, dusts, pastes or granules, are applied in a conventional manner, for example by spraying, atomizing, dusting, scattering, dressing or watering.

Examples of such formulations are:
I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained:

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis (thiocarbamyl disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal, piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole, 1-[2-(2,4-dichlorophenyl -4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)butan-2-one,
1-(4-chlorophenoxy)-3,3-dimethyl-1-(1H-1,2,4-triazol-1-yl)butan-2-ol,
1-(4-phenylphenoxy)-3,3-dimethyl-1-(1H-1,2,4-triazol-1-yl)-2-butanol,
α-(2-chlorophenyl)-α(4-chlorophenyl -5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

For the following experiments, the prior art active ingredient N-trichloromethylthiotetrahydrophthalimide (A) was used for comparison purposes.

USE EXAMPLE 1

Action on *Phytophthora infestans* in tomatoes

Leaves of potted tomatoes of the "Grosse Fleischtomate" variety were sprayed with aqueous liquors containing (dry basis) 80% of active ingredient and 20% of emulsifier. After the sprayed-on layer had dried, the leaves were infected with a zoospore suspension of *Phytophthora infestans*. The plants were then placed for 5 days in a water vapor-saturated chamber kept at 16° to 18° C. After this period, the disease had spread on the untreated control plants to such an extent that the fungicidal action of the compounds was able to be assessed.

The results of this experiment show that compound 1, applied as a 0.025 and 0.006% spray liquor, had a better fungicidal action (97%) than prior art active ingredient A (80%).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that active ingredient 1, when applied as a 0.05 and 0.0125% spray liquor, had a good fungicidal action (100%).

USE EXAMPLE 3

Action on powdery mildew of wheat

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of powdery mildew of wheat (*Erysiphe graminis* var. tritici). The test plants were then placed in a greenhouse at from 20° to 22° C. and from 75 to 80% relative humidity. After 7 days, the extent of powdery mildew spread was determined.

The results show that, when used as a liquor containing the active ingredient in a concentration of 0.025, 0.006 and 0.0015%, compound 1 had a good fungicidal action (100%).

USE EXAMPLE 4

Action on *Pyrenophora teres*

Leaves of barley seedlings of the Asse variety, in the two-leaf stage, were sprayed to runoff with an aqueous spray liquor containing (dry basis) 80% of active ingredient and 20% of emulsifier. After 24 hours the plants were inoculated with a spore suspension of *Pyrenophora teres*, and cultivated further for 48 hours in a cabinet at 18° C. and a high relative humidity. The plants were then kept for a further 5 days in the greenhouse at 20° to 22° C. and 70% relative humidity. The spread of the symptoms was then assessed.

The results show that, when used as a liquor containing the active ingredient in a concentration of 0.05%, for example compound 1 had a good fungicidal action (100%).

We claim:

1. An acrylic acid derivative of the formula:

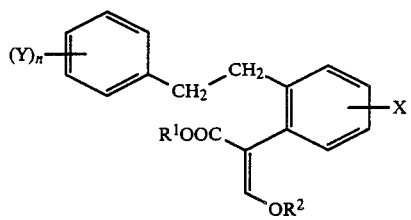

wherein $R^1$ and $R^2$ independently of one another are each $C_1$–$C_8$-alkyl; X is hydrogen, halogen, $C_1$–$C_4$-alkoxy, trifluoromethyl, cyano or nitro; y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, nitro, alkylthio, thiocyanato, cyano, or a group of the formula:

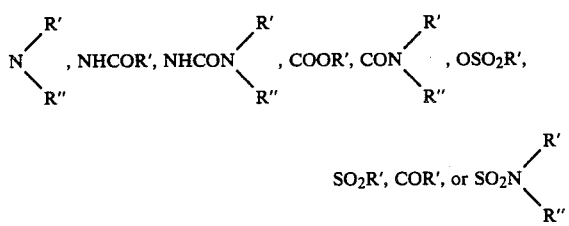

wherein R' and R" independently of one another are each hydrogen, alkyl, alkoxy, alkylthio or cycloalkyl or are each phenyl which is unsubstituted or substituted by alkyl, halogen or alkoxy, and n is from 1 to 4.

2. The acrylic acid derivative of claim 1, wherein Y is hydrogen, $C_1$–$C_{12}$ alkyl, halo-$C_1$–$C_4$-alkyl, $C_1$–$C_4$ alkoxy-$C_1$–$C_4$-alkyl, $C_5$–$C_8$ cycloalkyl, benzyl, phenyl, phenoxy, halogen, an unsubstituted $C_4H_4$ chain which is fused to the benzene radical to form naphthyl ring, $C_1$–$C_6$ alkoxy, halo-$C_1$–$C_4$-alkoxy, nitro, $C_1$–$C_4$-alkylthio, thiocyanato, cyano or a group of the formula:

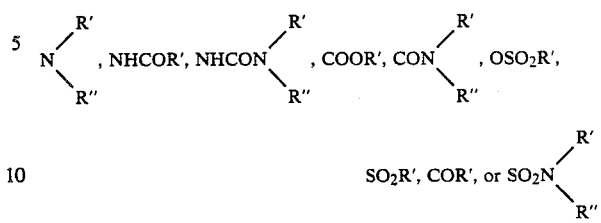

and wherein R' and R" independently of one another are each hydrogen, $C_1$–$C_4$-alkyl, $C_1$–$C_4$-alkoxy, $C_1$–$C_4$-alkylthio or $C_5$–$C_8$-cycloalkyl or are each phenyl which is unsubstituted or substituted by $C_1$–$C_4$-alkyl, halogen or $C_1$–$C_4$-alkoxy.

3. A fungicidal composition, comprising an effective amount of one or more compounds as set forth in claim 1 and a carrier.

4. A process for combating fungi, which comprises treating fungi, plants, seeds or soil or a combination thereof by adding thereto a fungicidally effective amount of one or more compounds as set forth in claim 1.

5. A process for combating fungi, which comprises treating fungi, plants, seeds or soil or a combination thereof by adding thereto a fungicidally effective amount of the composition of claim 3.

6. The compound, methyl α-(2-phenethylphenyl)-β-methoxyacrylate.

7. A fungicidal composition, comprising an effective amount of the compound of claim 6 and a carrier.

8. The fungicidal composition according to claim 3, wherein said composition comprises from 0.5 to 90% by weight of said acrylic acid fungicidal compound.

9. The process according to claim 4, wherein said fungicidally effective amount is from about 0.05 up to 3 kg or more of acrylic acid fungicidal compound per ha.

* * * * *

Adverse Decisions In Interference

Patent No. 4,782,177, Ulrich Schirmer, Stefan Karbach, Ernst-Heinrich Pommer, Eberhard Ammermann, Wolfgang Steglich, Barbara A. M. Schwalge, Timm Anke, ACRYLIC ACID DERIVATIVES AND FUNGICIDES WHICH CONTAIN THESE COMPOUNDS, Interference No. 102,847, final judgment adverse to the patentees rendered April 16, 1998 as to claims 1-9.
*(Official Gazette July 7, 1998)*